US006725231B2

(12) United States Patent
Hu et al.

(10) Patent No.: US 6,725,231 B2
(45) Date of Patent: Apr. 20, 2004

(54) DICOM XML DTD/SCHEMA GENERATOR

(75) Inventors: Jingkun Hu, Nyack, NY (US); Kwok Pun Lee, Yorktown Heights, NY (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 319 days.

(21) Appl. No.: 09/818,716

(22) Filed: Mar. 27, 2001

(65) Prior Publication Data

US 2002/0143727 A1 Oct. 3, 2002

(51) Int. Cl.$^7$ .......................... G06F 17/30; G06F 7/00; G06F 17/00
(52) U.S. Cl. ........................................... 707/102; 707/1
(58) Field of Search ..................... 707/1, 102

(56) References Cited

U.S. PATENT DOCUMENTS

| | | | | | |
|---|---|---|---|---|---|
| 5,893,109 | A | * | 4/1999 | DeRose et al. | 707/104.1 |
| 6,101,407 | A | * | 8/2000 | Groezinger | 600/407 |
| 6,260,021 | B1 | * | 7/2001 | Wong et al. | 705/2 |
| 2001/0051881 | A1 | * | 12/2001 | Filler | 705/3 |
| 2002/0111932 | A1 | * | 8/2002 | Roberge et al. | 707/1 |

OTHER PUBLICATIONS

U.S. patent application Ser. No. 09/686,401, Tirado–Ramos et al., filed Oct. 10, 2000.
Concurrently filed., "DICOM to XML Generator", Kwon Pun Lee et al, Docket US010071, Mar. 27, 2000.
*Supplement 23: Structured Reporting Storage SOP Classes* to the DICOM Standard, published by the DICOM Standards Committee, 1300 N. 17$^{th}$ Street, Rosslyn, VA 22209 USA.
*XML Schema Part 0: Primer* W3C Candidate Recommendation Oct. 24, 2000. ©2000 W3C® (MIT, INRIA, Keio).

* cited by examiner

Primary Examiner—Wayne Amsbury
Assistant Examiner—Cindy Nguyen
(74) Attorney, Agent, or Firm—Gregory L. Thorne

(57) ABSTRACT

A DICOM-to-XML conversion system is provided that converts the DICOM SR standard into a set of XML DTDs and Schemas. By providing a mapping between the DICOM SR standard and XML DTDs and Schemas, DICOM specific XML-based applications can be developed, via a larger field of XML-fluent application developers. Additionally, by providing standard XML DTDs and Schemas for containing DICOM data, other commonly available non-DICOM-related applications, such as accounting and mailing programs, can be structured to use information as required from DICOM reports that are converted to conform to these defined XML DTDs and Schemas. In a preferred embodiment, a two-phase conversion is employed. The DICOM SR specification is parsed and converted directly into a set of "raw" XML documents. Thereafter, the "raw" XML documents are transformed into the corresponding XML DTDs and Schemas, via an XSLT processor. Changes to the desired XML DTDs and Schemas, as standards develop, can thus be effected via changes in the corresponding XSLT stylesheets, without modification to the DICOM-to-raw-XML process.

15 Claims, 9 Drawing Sheets

| SR DOCUMENT SERIES MODULE ATTRIBUTES | | | |
|---|---|---|---|
| Attribute Name | Tag | Type | Attribute Description |
| Modality | (0008,0060) | 1 | Modality type. Enumerated Value: SR = SR Document |
| Series Instance UID | (0020,000E) | 1 | Unique identifier of the Series. Note: No SR-specific semantics are specified. |
| Series Number | (0020,0011) | 1 | A number that identifies the Series. Note: No SR-specific semantics are specified. |
| Referenced Study Component Sequence | (0008,1111) | 2 | Uniquely identifies the Performed Procedure Step SOP Instance for which the Series is created. ... |
| >Referenced SOP Class UID | (0008,1150) | 1C | Uniquely identifies the referenced SOP Class... |
| >Referenced SOP Instance UID | (0008,1155) | 1C | Uniquely identifies the referenced SOP Instance... |

```
<module_attributes>
    <name>sr_document_series_module</name>
    <atomic_attribute>
        <name>modality</name>
        <tag>0008,0060</tag>
        <type>1</type>
        <description>modality type, Enumerated value: SR = SR Document
        </description>
    </atomic_attribute>
    ...
    <sequence_attribute>
        <name>referenced_component_study_sequence</name>
        <tag>008,1111</tag>
        <type>2</type>
        <description>Uniquely identifies ... </description>
        <atomic_attribute>
            <name>Referenced_SOP_Class_UID</name>
            <tag>0008,1150</tag>
            ...
    ...
```

FIG. 4

```
                                              910
<xsl:template match="iod_module">
    <element>
        <xsl:attribute name="name">      911
            <xsl:value-of select="name"/>
        </xsl:attribute>       912
        <complexType>
            <sequence>          913
                <xsl:for-each select="ie">
                    <element>
                        <xsl:attribute name="name">    914
                            <xsl:value-of select="name"/>
                        </xsl:attribute>
                        <complexType>
                            <sequence>           915
                                <xsl:for-each select="module">
                                    <element>
                                        <xsl:attribute name="name">    916
                                            <xsl:value-of select="name"/>
                                        </xsl:attribute>         917
                                        <xsl:attribute name="type">
                                            <xsl:value-of select="name"/>_type
                                        </xsl:attribute>         918          919
                                        <xsl:if test="usage='U|C'">
                                            <xsl:attribute name="minOcurrs">0</xsl:attribute>
                                        </xsl:if>
                                    </element>
                                </xsl:for-each>
                            </sequence>
                        </complexType>
                    </element>
                </xsl:for-each>
            </sequence>
        </complexType>
    </element>
</xsl:template>
```

```
                              920
<xsl:template match="module_attributes">
    <complexType>
        <xsl:attribute name="name">        ──── 921
            <xsl:value-of select="name"/>_type
        </xsl:attribute>
        <sequence>                              ──── 922
            <xsl:for-each select="atomic_attribute">
                <element>
                    <xsl:attribute name="ref">
                        <xsl:value-of select="name"/>
                    </xsl:attribute>
                    <xsl:if test="type='1C|2C|3'">
                        <xsl:attribute name="minOccurs">0</xsl:attribute>
                    </xsl:if>
                </element>
            </xsl:for-each>                          ──── 923
            <xsl:for-each select="sequence_attribute">
                <element>
                    <xsl:attribute name="ref">
                        <xsl:value-of select="name"/>
                    </xsl:attribute>
                    <xsl:if test="type='1C|2C|3'">
                        <xsl:attribute name="minOccurs">0</xsl:attribute>
                    </xsl:if>
                </element>
            </xsl:for-each>
        </sequence>                        ╱ 924
    </complexType>                        ╱
    <xsl:call-template name="atomic_attribute_element"/>    ╱ 925
    <xsl:call-template name="sequence_attribute_element"/>
</xsl:template>
```

```
<xsl:template name="atomic_attribute_element">
    <xsl:for-each select="atomic_attribute">
        <element>
            <xsl:attribute name="name">
                <xsl:value-of select="name"/>
            </xsl:attribute>
            <complexType>
                <simpleContent>
                    <extension>
                        <xsl:attribute name="base">
                            <xsl:call-template name="data_type_select"/>
                        </xsl:attribute>
                        <attribute>
                            <xsl:attribute name="name">codingScheme</xsl:attribute>
                            <xsl:attribute name="value">DICOM</xsl:attribute>
                        </attribute>
                        <attribute>
                            <xsl:attribute name="name">codeID</xsl:attribute>
                            <xsl:attribute name="value">
                                <xsl:value-of select="tag"/>
                            </xsl:attribute>
                        </attribute>
                    </extension>
                </simpleContent>
            </complexType>
        </element>
    </xsl:for-each>
</xsl:template>
```

```
<xsl:template name="sequence_attribute_element">
    <xsl:for-each select="sequence_attribute">
        <element>
            <xsl:attribute name="name"><xsl:value-of select="name"/></
xsl:attribute>
            <attribute>
                <xsl:attribute name="name">codingScheme</xsl:attribute>
                <xsl:attribute name="value">DICOM</xsl:attribute>
            </attribute>
            <attribute>
                <xsl:attribute name="name">codeID</xsl:attribute>
                <xsl:attribute name="value">
                    <xsl:value-of select="tag"/>
                </xsl:attribute>
            </attribute>
            <xsl:if test="count(child::atomic_attribute)!=0">
                <sequence>
                    <xsl:call-template name="atomic_attribute_element"/>
                </sequence>
            </xsl:if>
        </element>
    </xsl:for-each>
    ...
</xsl:template>
```

```
<complexType name="sr_document_series_module_type">
    <sequence>        ⎯621
        <element ref="modality"/>        ＼610
        <element ref="series_instance_uid"/>
        <element ref="series_number"/>
        <element ref="referenced_study_component_sequence"/>
    </sequence>
</complexType>        ＼624
    ...        ⎯621
<element name="modality">
    <complexType>
        <simpleContent>
            <extension base="modality_value">
                <attribute name="codingScheme" value="DICOM"/>
                <attribute name="codeId" value="0008,0060"/>
            </extension>        ＼631
        </simpleContent>
    </complexType>
</element>
    ...
```

FIG. 10

```
1110＼                                            ⎯1115
<simpleType name="AS-0">
    <restriction base="string"><pattern value="[0-9]{3}[DWMY]"/></restriction>
</simpleType>  1120＼                          ⎯1125
<simpleType name="AS-1">
    <restriction base="AS-0"><minLength value="4"/></restriction>
</simpleType>            ＼1110'
<simpleType name="CS-0">
    <restriction base="string"><maxLength value="16"/></restriction>
</simpleType>
<simpleType name="CS-1">
    <restriction base="string"><maxLength value="16"/><minLength value="1"/>
    </restriction>
</simpleType>
```

FIG. 11

DICOM XML DTD/SCHEMA GENERATOR

BACKGROUND OF THE INVENTION

1. Field of the Invention

This invention relates to the field of modeling and data representation, and in particular to the modeling and representation of medical reports, via the use of DICOM SR relational data.

2. Description of Related Art

The Digital Imaging and Communications in Medicine (DICOM) Structured Reporting (SR) standard, and the SR Documentation Model upon which it is based, improves the expressiveness, precision, and comparability of documentation of diagnostic images and waveforms. DICOM SR supports the interchange of expressive compound reports in which the critical features shown by images and waveforms can be denoted unambiguously by the observer, indexed, and retrieved selectively by subsequent reviewers. Findings may be expressed by the observer as text, codes, and numeric measurements, or via location coordinates of specific regions of interest within images or waveforms, or references to comparison images, sound, waveforms, curves, and previous report information. The observational and historical findings recorded by the observer may include any evidence referenced as part of an interpretation procedure. Thus, DICOM SR supports not only the reporting of diagnostic observations, but the capability to document fully the evidence that evoked the observations. This capability provides significant new opportunities for large-scale collection of structured data for clinical research, training, and outcomes assessment as a routine by-product of diagnostic image and waveform interpretation, and facilitates the pooling of structured data for multi-center clinical trials and evaluations.[1]

[1] "Clinical Rationale for the SR Documentation Model and the DICOM Structured Reporting (SR) Standard", Abstract, W. Dean Bidgood, Jr., © 1999.

The DICOM SR is based on a relational data technology, and has been standardized by the National Electrical Manufacturers Association (NEMA). *Supplement 23: Structured Reporting Storage SOP Classes* to the DICOM Standard, published by the DICOM Standards Committee, 1300 N. 17th Street, Rosslyn, Va. 22209 USA, and incorporated by reference herein, introduces the SR Service-Object Pair (SOP) Classes for transmission and storage of documents that describe or refer to any number of images or waveforms or to the specific features that they contain. This standard is expected to be adopted by the medical equipment manufacturers and providers at large to provide text, image, and waveform content in a structured reporting format.

Although the DICOM SR standard provides for a consistent reporting and recording scheme, the use of the information contained in a DICOM SR is limited to DICOM compliant applications that can process this information using the DICOM specific format. Application developers must be DICOM literate, and a methodology for deploying applications that interoperate with other applications outside the DICOM domain has not yet been developed.

In the computer industry, progress has been made in the use of standardized languages and methodologies that facilitate the use of information from a variety of sources by a variety of applications. A standard language that is widely used for processing content material is the World Wide Web Consortium Extensible Markup Language (XML), which is derived from the Standard Generalized Markup Language (SGML), and is designed to describe data and its structure so that it can be easily transferred over a network and consistently processed by the receiver. Because XML is used to describe information as well as structure, it is particularly well suited as a data description language. One of XML's particular strengths is that it allows entire industries, academic disciplines, and professional organizations develop sets of Document Type Definitions (DTDs) and Schemas that can serve to standardize the representation of information within those disciplines. Given a set of DTDs and Schemas, content material that is modeled in conformance with the DTDs and Schemas can be processed by applications that are developed for these DTDs and Schemas.

A further advantage of the use of XML is the wealth of tools that are available for the processing of XML-compatible data. Of particular significance, the "Extensible Stylesheet Language" (XSL) is a language for expressing stylesheets, and the "XSL Transformations" (XSLT) is a language for transforming XML documents into other XML documents, using stylesheets. A stylesheet contains a set of template rules, which are used to match a pattern to a source document, or "source tree" and, when the appropriate match is found, to instantiate a template to a result document, or "result tree". In this manner, XML information that is structured for one application can be relatively easily transformed into a different structure for another application.

BRIEF SUMMARY OF THE INVENTION

Although XML may be considered a relatively new and specialized language, it can be expected that more programmers and other computer professionals will be familiar with XML than those who are familiar with DICOM. Additionally, it can be expected that more general-purpose utilities and applications will be available for use on XML encoded information than will be available for use on DICOM SR encoded information.

An objective of this invention, therefore, is to provide a method and system that facilitate the creation of XML Document Type Definitions (DTDs) and XML Schemas that correspond to the DICOM SR standard. A further objective of this invention is to provide a method and system for creating an XML representation of DICOM objects that is flexible and extensible.

These objectives and others are achieved by providing a conversion system that converts the DICOM SR standard into a set of XML DTDs and Schemas. By providing a mapping between the DICOM SR standard and XML DTDs and Schemas, DICOM specific XML-based applications can be developed, via a larger field of XML-fluent application developers. Additionally, by providing standard XML DTDs and Schemas for containing DICOM data, other commonly available non-DICOM-related applications, such as accounting and mailing programs, can be structured to use information as required from DICOM reports that are converted to conform to these defined XML DTDs and Schemas. In a preferred embodiment, a two-phase conversion is employed. The DICOM SR specification is parsed and converted directly into a set of "raw" XML documents. Thereafter, the "raw" XML documents are transformed into the corresponding XML DTDs and Schemas, via an XSLT processor. Changes to the desired XML DTDs and Schemas, as standards develop, can thus be effected via changes in the corresponding XSLT stylesheets, without modification to the DICOM-to-raw-XML process.

BRIEF DESCRIPTION OF THE DRAWINGS

The invention is explained in further detail, and by way of example, with reference to the accompanying drawings wherein:

FIG. 4 illustrates an example conversion of a DICOM Module attribute table into an XML document in accordance with this invention.

FIG. 6 illustrates an example XSLT file for transforming an XML 10D document into an XML Schema in accordance with this invention.

FIG. 7 illustrates an example XSLT file for transforming an XML module document into an XML Schema in accordance with this invention.

FIG. 8 illustrates an example XSLT file for transforming an XML atomic attribute element for use in an XML Schema in accordance with this invention.

FIG. 9 illustrates an example XSLT file for transforming an XML sequence attribute element for use in an XML Schema in accordance with this invention.

FIG. 10 illustrates an example XML Schema corresponding to the example DICOM Module attribute table of FIG. 4 in accordance with this invention.

FIG. 11 illustrates an example XML Schema of data types in accordance with this invention.

Throughout the drawings, the same reference numerals indicate similar or corresponding features or functions.

DETAILED DESCRIPTION OF THE INVENTION

As noted above, although applications can be developed that utilize DICOM's relational structured reporting scheme directly, it can be expected that the number of programmers and other computer professions who are familiar with XML and object-oriented technologies and techniques will be substantially greater than those who are familiar with DICOM and relational technologies and techniques.

Copending U.S. patent application "UML MODEL AND XML REPRESENTATIONS OF DIGITAL IMAGING AND COMMUNICATIONS IN MEDICINE STRUCTURED REPORTS (DICOM SR)", Ser. No. 09/686,401, filed Oct. 10, 2000 for Alfredo-Tirado Ramos, Jingkun Hu, and Yasser alSafadi, incorporated by reference herein, discloses a system and method for transforming the DICOM SR specification into a UML (Unified Modeling Language) model to facilitate an understanding of the DICOM SR by non-DICOM systems analysts and system designers. The system and method also includes a transformation of this UML model into XML Document Type Definitions (DTDs) and XML Schemas. The system and method also includes a transformation of a DICOM SR report into a UML document, and further includes a transformation of the UML document into an XML document. Although this system and method is particularly well suited for conveying an understanding of DICOM SR to non-DICOM professionals, and facilitates the development of XML application programs, the transformation of DICOM SR reports to XML via a UML transformation introduces an intermediate level of abstraction. This additional level of model-abstraction may result in a loss of information, because the UML modeling language is primarily designed to model structures and interactions, not data.

Concurrently filed U.S. patent application "DICOM TO XML GENERATOR", Ser. No. 09/818,715, filed Mar. 27, 2001 for Kwok Pun Lee and Jingkun Hu, and incorporated by reference herein, discloses a system and method for transforming the DICOM SR data files directly into XML documents, using XML stylesheets that contain templates corresponding to XML Document Type Definitions (DTDs) and XML Schemas, such as the DTDs and Schemas provided by the invention that is disclosed herein.

This invention is based on the premise that DICOM-related application programs will be developed as XML-enabled applications, and that, to facilitate such development, DICOM XML DTDs and Schemas that correspond to the DICOM SR specification will be required.

Figure 1:
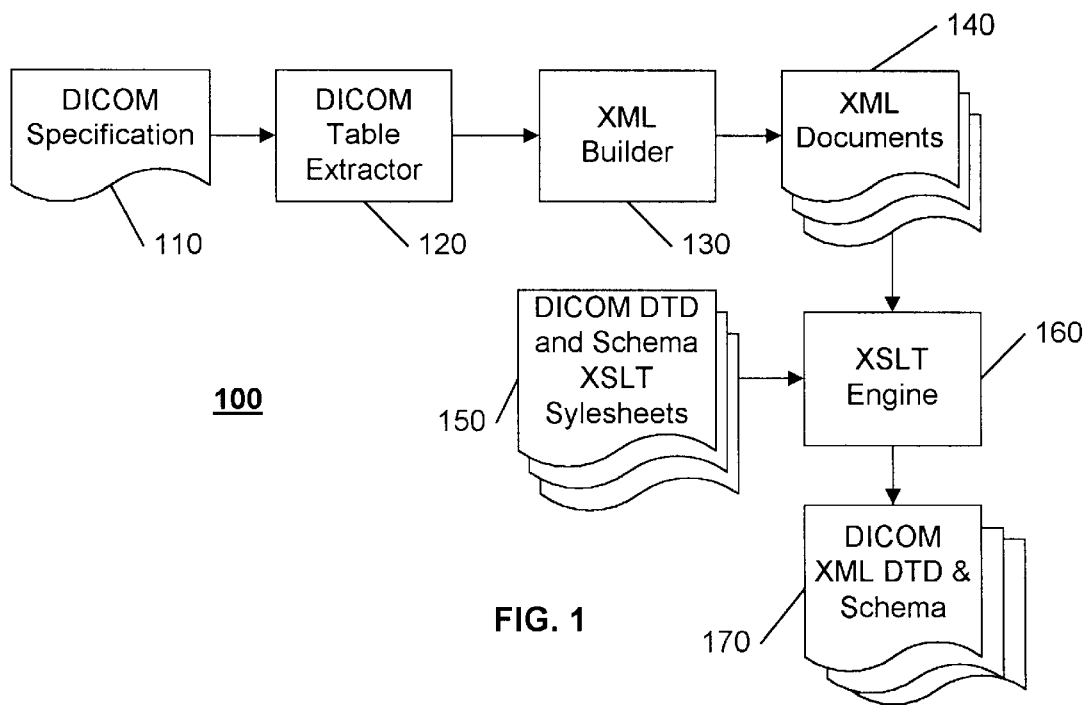
FIG. 1 illustrates an example block diagram of a DICOM specification to XML DTD/Schema conversion system in accordance with this invention

FIG. 1 illustrates an example block diagram of a DICOM to XML conversion system 100 in accordance with this invention. The conversion system 100 transforms a DICOM specification 110 into a corresponding set of XML DTDs and Schemas 170. A DICOM table extractor 120 extracts the information from the DICOM input specification 110, and provides the parsed information to an XML builder 130. In the DICOM environment, the DICOM SR specification is available in electronic form, for example, in a ".pdf" file that is available from an Internet site, and the pertinent information is contained in a set of tables, such as those illustrated as 110a, 110b, 110c in FIGS. 3–5, discussed further below.

In a preferred embodiment, the XML builder 130 is configured to effect a straightforward translation of each DICOM table, using fairly straightforward rules, discussed further below, but without consideration for the particular format or structure required by an application program that is intended to use the DICOM-XML DTDs and Schemas. Alternatively, the XML builder 130 may be configured to format the DICOM-XML DTDs and Schemas into a form that is designed for use in a particular application. By partitioning the Table-to-XML conversion from the XML-formatting task, the resultant system is expected to be more flexible and robust than a composite system, consistent with the principles of well structured designs. For ease of reference, the directly-translated XML documents from the XML builder 130 are herein referred to as "raw" XML documents and data.

In a preferred embodiment, the raw XML documents are processed via an XSLT (Extensible Stylesheet Language Transformation) engine 160. The additional advantage of segregating the XML-conversion from the XML-formatting is that existing XML-transformation tools and techniques can be used to effect the desired output XML format structure. In this preferred use of XSLT, the desired output XML format is specified using XSLT stylesheets 150. These stylesheets 150 are defined based on the format of the DICOM-XML DTDs and Schemas that is intended to be used for the development of one or more application programs. If a DICOM-XML standard is adopted for DICOM processing applications, then the use of stylesheets 150 that are compatible with this standard will allow the DICOM-XML DTDs and Schemas that are produced by the conversion system 100 to be used in the development of each application that is compatible with the standard. If a variety of DICOM-XML formats are defined, a different set of stylesheets 150 can be provided for each format, and thereby allowing the use of the same builder 130, regardless of the particular output format.

Figure 2:
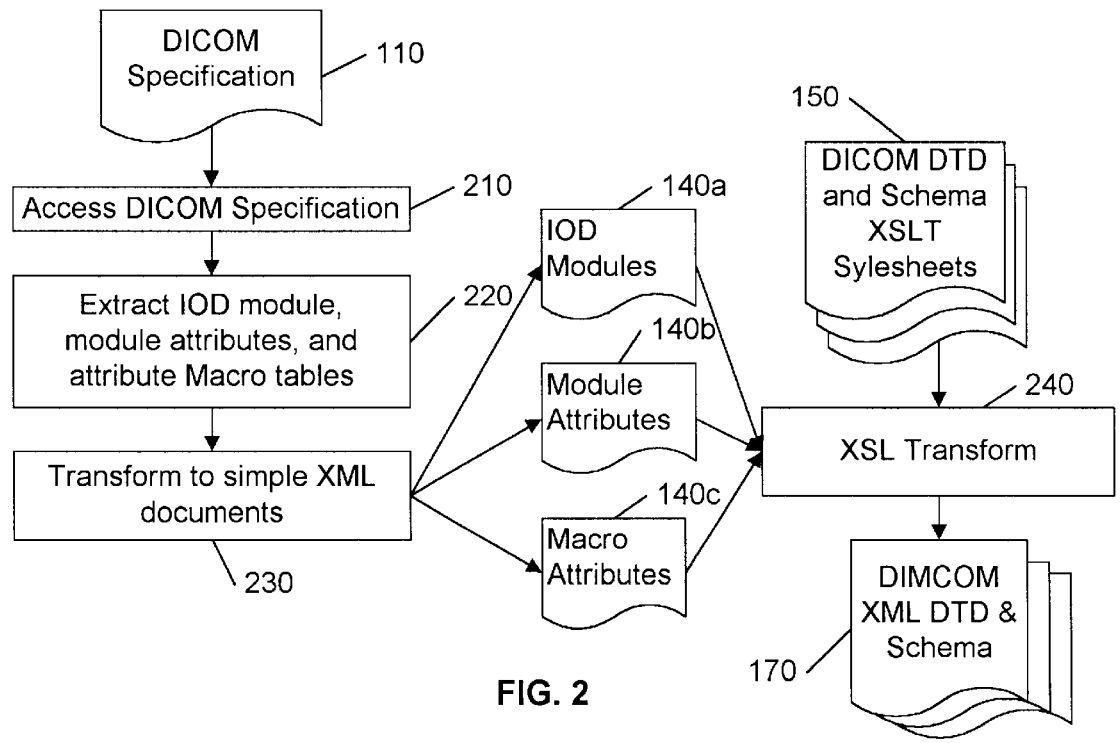
FIG. 2 illustrates an example flow diagram for converting a DICOM specification into an XML DTD/Schema in accordance with this invention.
Figure 5:
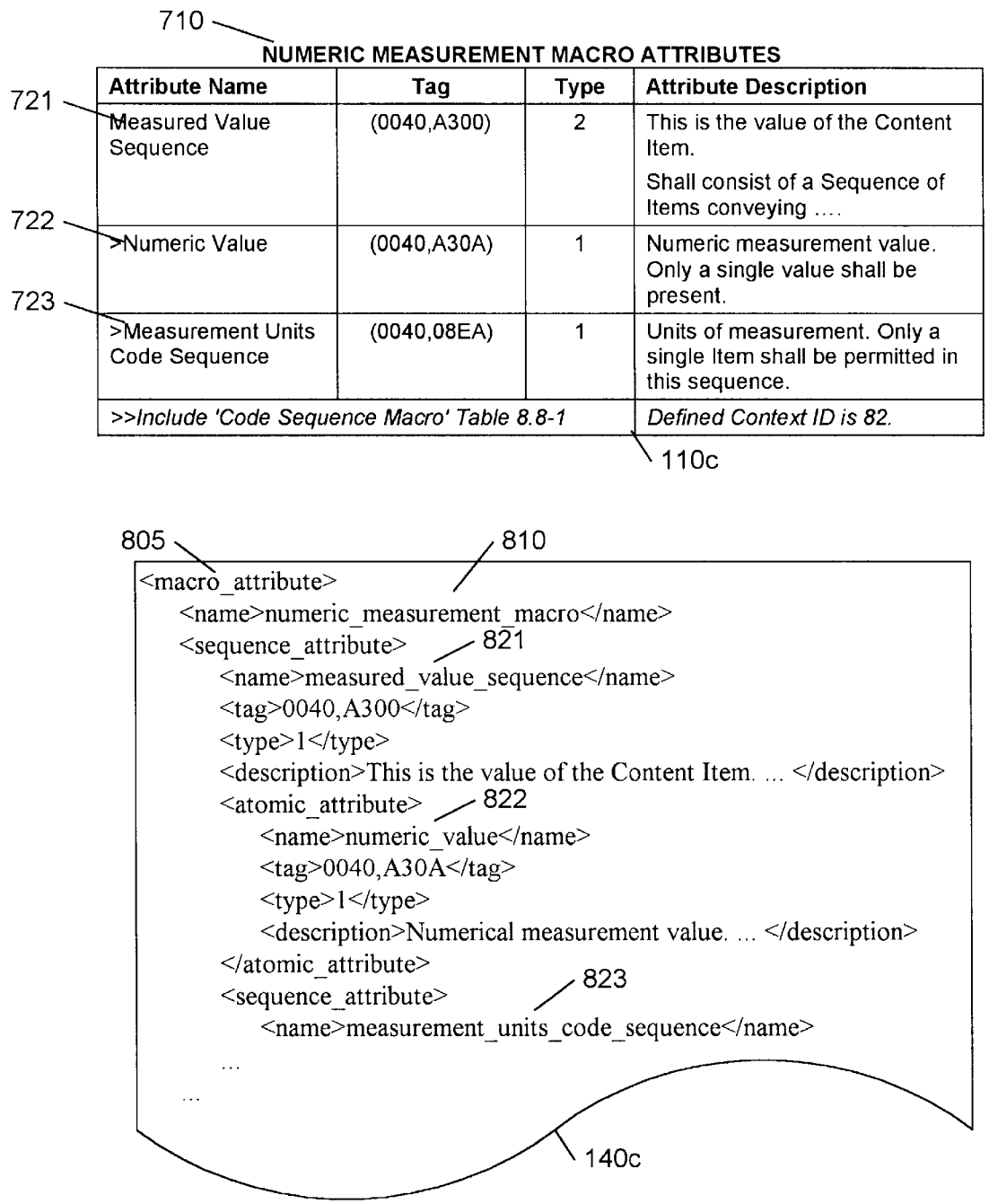
FIG. 5 illustrates an example conversion of a DICOM Macro attribute table into an XML document in accordance with this invention.

FIG. 2 illustrates an example flow diagram of a DICOM to XML conversion system 100 in accordance with this invention. The DICOM specification 110 is accessed, at block 210, and the tables within the specification 110 are extracted, at block 220. Generally, three types of tables are contained in the specification. These table types include: IOD (Information Object Definition) Module tables, Module Attributes tables, and Macro Attributes tables. In a preferred embodiment of this invention, each extracted table is temporarily stored as a separate document (not illustrated), for subsequent processing, although in-line processing, without an intermediate document storage is also feasible. An example IOD Module table 110a is illustrated in FIG. 3; an example Module Attributes table 110b is illustrated in FIG. 4; and an example Macro Attributes table 110c is illustrated in FIG. 5.

Each table in the specification 110 is encoded as a corresponding XML document 140, at the block 230 in FIG. 2, corresponding to the XML builder 130 in FIG. 1. The functions performed at the block 230 in FIG. 2 depend upon the type of DICOM table 110 being processed, and are best described with reference to the example transformations illustrated in FIGS. 3–5. For all tables, the XML element names are derived from the entries in the tables. All characters in the table entries corresponding to element names are converted to lower case; each space, hyphen, and slash is replaced by an underscore; and all brackets and apostrophes are removed.

Figure 3:
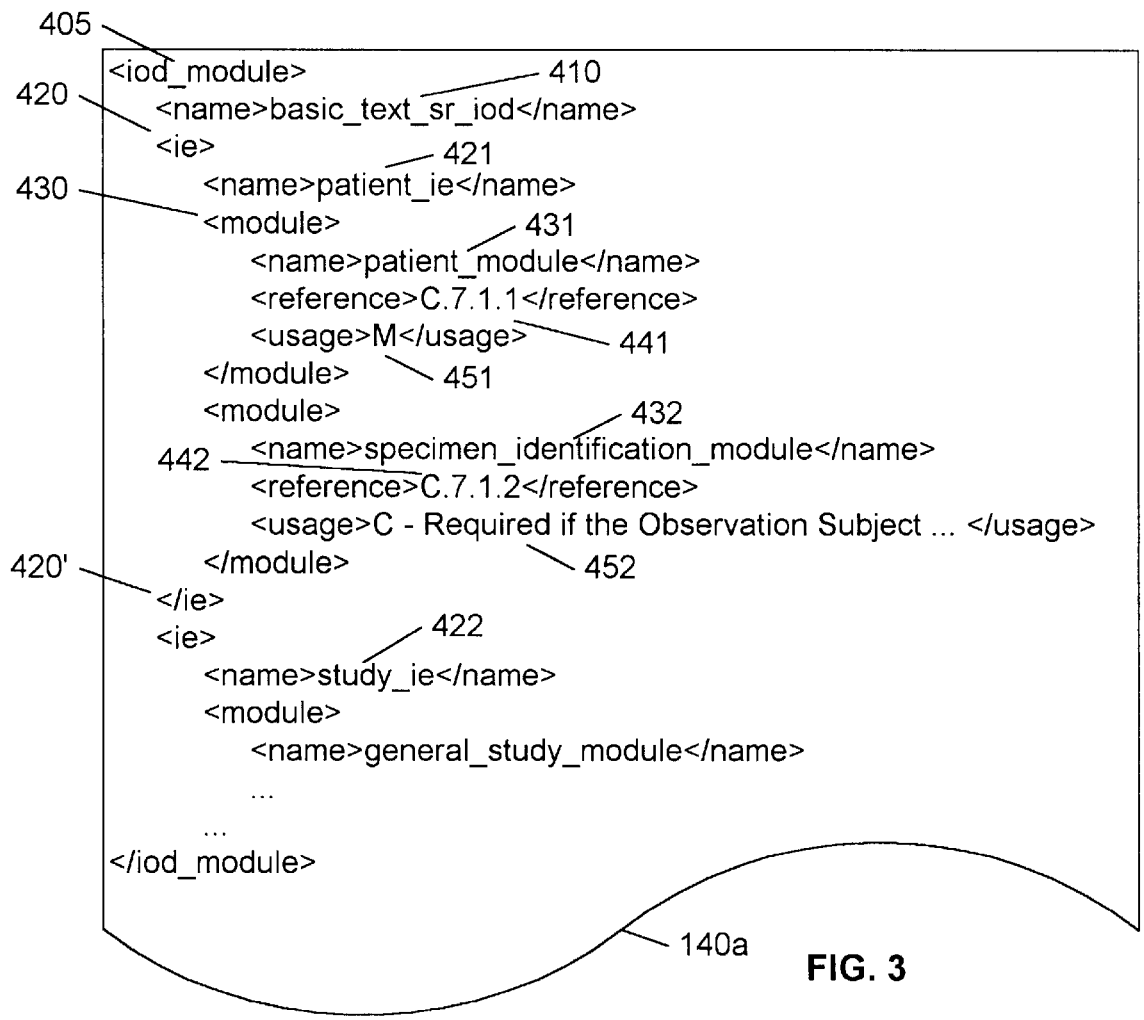
FIG. 3 illustrates an example conversion of a DICOM Information Object Definition (10D) table into an XML document in accordance with this invention.

An IOD Modules table 10a is converted to an XML document 140a using the following rules, as illustrated in FIG. 3:

The root of the XML document 140a is named "iod_ module" 405, and contains a "name" element 410 that is derived from that table title 310.

An "_ie" suffix is appended to each IE (Information Entity) 321, 322, to form a name 421, 422 for each corresponding XML "ie" element 420. As is required in XML, the content of each element is contained within bounds marked by "<elementname>" 420 and "</elementname>" 420' XML element identifiers.

A "_module" suffix is appended to each DICOM module 330 identifier 331, to form a name 431 for each corresponding XML "module" element 430. The XML "module" element 430 contains three XML elements titled "name", "reference", and "usage".

The contents of these elements 431, 441, 451, and 432, 442, 452, are taken from the table entries 331, 341, 351, and 332, 342, 352.

In like manner, a Module Attributes table 10b is converted to an XML document 140b using the following rules, as illustrated in FIG. 4.

The root of the XML document 140b is named "module_ attributes" 605, and contains a "name" element 610 that is derived from that table title 510.

Each DICOM attribute is mapped to an XML composite element that contains the name 620, tag, type, and description elements, corresponding to the columns 520 of the table 110b.

If the DICOM attribute is a primitive, or atomic attribute, it is identified as an XML atomic primitive 690, and the contents of the elements 621, 631, 641, 651 in the primitive 690 are taken from the table entries 521, 531, 541, 551.

If the DICOM attribute is a sequence attribute 524 that contains sub-attributes 525, a sequence attribute 695 that comprises sub-elements is formed. The XML name 624, tag 634, type, and description elements corresponds to the DICOM sequence name 524, tag 534, type, and description contained in the table 110b.

Each XML sub-element 625 of an XML sequence element 624 is formed as an atomic 690' or sequence attribute, using the above rules, recursively, for each DICOM sub-attribute 525.

The Macro Attributes table 110c is converted to an XML document 140c using the same rules as the Module Attributes table 110b, as illustrated by the conversion of the DICOM macros 721 and sub-macros 722, 723 into XML composite element 821 and sub-elements 822, 823 in FIG. 5. The root of the XML document 140c is named "macro_ attribute" 805, and contains a "name" element 810 that is derived from the table title 710.

Referring again to FIG. 2, after conversion of each table in the DICOM specification 110 to a corresponding XML document 140 (140a–c), the XSLT engine 160, which may be any of a variety of available XSLT engines, provides the desired XML DTD and Schema output formats. As is known in the art, XSLT is a language that facilitates the transformation of an XML document into another XML document, using template matching. The stylesheets 150 contain template pairs. The original XML document is searched for a pattern that matches the first template in the pair. When the search results in a match, the information at the match location in the original XML document is converted to the form of the second template in the pair, and provided to the output XML document. In the subject invention, the first template is configured to match the form of the information in the documents 140a–c, and the second template is configured to correspond to whatever format is desired for use in a particular application, or, as noted above, to an agreed-upon standard format, for compatibility among a variety of applications.

In a preferred embodiment of this invention, each XML document 140 is converted to an XML Schema 170, using XSLT stylesheets 150. Once the Schemas 170 are created, corresponding XML DTDs can be generated automatically, using conventional XML tools. XML Schemas support complex element types and a variety of data types, including integer, date, string, and so on, whereas XML DTDs only support simple structures and string data types. By providing the XML Schemas corresponding to the DICOM specification, the richness of the DICOM standard can be transformed to an XML-compatible form, with minimal information loss, if any.

FIGS. 6 through 9 illustrate example XSLT stylesheets 150a–d for creating XML Schemas 170 from the XML documents 140 as illustrated in FIG. 1. As noted, the XSLT language is conventionally used to effect format transformations, and alternative stylesheets will be evident to one of ordinary skill in the art. As also noted, the XML builder 130 may be structured to provide the desired XML Schema or DTD documents 170 directly, thereby obviating the need for the XSLT engine 160 and XSLT stylesheets 150.

FIG. 6 illustrates an example XSLT stylsheet 150a for transforming an XML IOD document (140a in FIG. 3) into an XML Schema in accordance with this invention. For each XML document matching the root name of an IOD module 910, a complex type element 912 is created having a name 911 that is extracted from the name attribute in the XML IOD document 140a. The element contains a sequence of IE elements 913. Each IE element 913 is transformed to a complex type element having the name 914 of the IE element in the XML IOD document 140*a*. Each IE element 913 contains a sequence of module elements 915. Each module element 915 is assigned a name 916 from the XML IOD document 140*a*, and contains a sequence of simple type or complex type elements, having values 917 that are extracted from the XML IOD document 140*a*. If the usage element 918 is a "U" or a "C", an attribute 919 called "minOccurs" with a value 0 is created.

In like manner, FIG. 7 illustrates an example XSLT stylesheet 150*b* for transforming an XML module document (140*b* in FIG. 4) into an XML Schema in accordance with this invention. For each XML document matching a Module description 920, a complex type element is created having a name 921 that is extracted from the document 140*b*. The complex type element includes a sequence of atomic attributes 922 and sequence attributes 923. Following the complex type, sub-templates 924 and 925 are called to provide the data corresponding to each element in the sequence. Example sub-templates 924 and 925 are illustrated in FIGS. 8 and 9, respectively.

FIG. 10 illustrates an example output of the XSLT stylesheet 150*b* of FIG. 7 when applied to the example document 140*b* of FIG. 4. Illustrated in FIG. 11 are corresponding items 610, 621, 624, and 631 of document 140*b* from FIG. 4, which correspond to items 510, 521, 524, and 531 of the original table 110*b* of FIG. 4 from the DICOM specification. Thus, as illustrated, an XML Schema is created, automatically, from a table 110 of a DICOM specification, using the above described processes and systems.

For completeness, FIG. 11 illustrates an example XML Schema for a variety of data types in accordance with this invention. The data type is defined from the tag value contained in the tables, based on the data dictionary of DICOM. For example, the tag "0008,0060", reference item 531 in FIG. 1, is defined as a "CS" data type (Coded String). Other data types include, for example "AS" (Age String). In the example of FIG. 11, the data type "AS-0" 1110 corresponds to an age string which may or may not have an assigned value, and the data type "AS-1" 1120 corresponds to an age string which must have an assigned value. The pattern value field 1115 defines the allowable characters in the age string AS-0 1110. The data type AS-1 1120 uses AS-0 as a base 1110', and adds a requirement of a minimum length to the age string. Similar codings for each of the other data types in DICOM will be evident to one of ordinary skill in the art in view of this disclosure.

The foregoing merely illustrates the principles of the invention. It will thus be appreciated that those skilled in the art will be able to devise various arrangements which, although not explicitly described or shown herein, embody the principles of the invention and are thus within the spirit and scope of the following claims.

We claim:

1. A method for mapping a DICOM specification into an XML document, comprising:
   mapping each entry of a DICOM table of the DICOM specification into a corresponding XML element of a plurality of XML elements,
   outputting each XML element of the plurality of XML elements to the XML document, in an output format that conforms to at least one of: an XML document-type-definition and an XML Schema.

2. The method of claim 1, wherein
   outputting each XML element includes
   formatting the XML element via one or more XSLT templates to conform to the output format.

3. The method of claim 2, wherein
   the formatting of the XML element is via an XSLT engine.

4. The method of claim 2, wherein
   the one or more XSLT templates includes a template that is configured to convert a set of XML elements of the plurality of XML elements from the DICOM table corresponding to at least one of:
      a DICOM Structured Reporting (SR) Information Object Description (IOD) table,
      a DICOM SR Module Attributes table, and
      a DICOM SR Macro Attributes table.

5. The method of claim 1, wherein
   the mapping of each entry into a corresponding XML element is substantially independent of the output format.

6. The method of claim 1, wherein the table corresponds to a DICOM IOD Module table, and the method further includes:
   forming an information entity element name for each DICOM Information Entity by adding a first suffix to a name of the Information Entity in the table,
   forming an module element name for each DICOM Module by adding a second suffix to a module identifier in the table, and
   forming a composite element that includes two XML elements for containing reference and usage data from the table for each DICOM Module.

7. The method of claim 1, wherein the table corresponds to at least one of: a DICOM Module Attributes table, and a DICOM Macro Attributes table, and the method further includes:
   mapping each DICOM attribute in the table to a composite element for containing attribute name, tag, type, and attribute description data from the table.

8. The method of claim 7, further including:
   mapping each DICOM non-sequence attribute into an XML composite atomic element, and
   mapping each DICOM sequence attribute into an XML composite sequence element.

9. The method of claim 8, further including:
   recursively mapping each sub-element of each DICOM sequence attribute into at least one of: an XML composite atomic element and an XML composite sequence element.

10. A DICOM to XML conversion system that comprises:
   a DICOM table extractor that is configured to provide a plurality of table entries from a DICOM specification,
   an XML transformer, operably coupled to the DICOM table extractor, that is configured to provide a plurality of XML elements corresponding to the plurality of table entries.

11. The DICOM to XML conversion system of claim 10, wherein
   the XML transformer is configured to provide the plurality of XML elements in an output format that conforms to at least one of: an XML document-type-definition and an XML Schema.

12. The DICOM to XML conversion system of claim 11, wherein
   the XML transformer includes an XSLT engine that is configured to provide the plurality of XML elements based on one or more XSLT stylesheet templates that conform to the output format.

13. The DICOM to XML conversion system of claim 12, wherein the XML transformer further includes:

an XML builder, operably coupled to the DICOM table extractor, that is configured to effect a direct mapping of each entry of the plurality of table entries into a corresponding XML element of the plurality of XML elements, substantially independent of the output format.

14. The DICOM to XML conversion system of claim 13, wherein the table entries correspond to entries in at least one of: an IOD Module table, a Module Attribute table, and a Macro Attribute table.

15. The DICOM to XML conversion system of claim 14, wherein the XML builder is configured to provide an XML document corresponding to each of the at least one of: the IOD Module table, the Module Attribute table, and the Macro Attribute table.

* * * * *